United States Patent
Rouns et al.

(10) Patent No.: US 6,923,786 B2
(45) Date of Patent: Aug. 2, 2005

(54) SILICONE ELASTOMER MATERIAL FOR USE WITH ENTERIC FEEDING DEVICE

(75) Inventors: Cameron G. Rouns, South Jordan, UT (US); Don J. McMichael, South Jordan, UT (US); Michael A. Kenowski, Pocatello, ID (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 471 days.

(21) Appl. No.: 09/733,161

(22) Filed: Dec. 8, 2000

(65) Prior Publication Data

US 2002/0193753 A1 Dec. 19, 2002

Related U.S. Application Data

(60) Provisional application No. 60/170,000, filed on Dec. 9, 1999.

(51) Int. Cl.[7] ............................................. A61M 37/00
(52) U.S. Cl. .................................. 604/93.01; 604/96.01
(58) Field of Search ........................... 604/93.01, 95.03, 604/96.01, 97.01, 101.01, 101.03, 101.05, 102.01, 102.02, 102.03, 103.03, 523, 916, 27, 41, 48, 99.01, 99.02, 103, 175, 257, 264, 901, 915, 912

(56) References Cited

U.S. PATENT DOCUMENTS

| | | | |
|---|---|---|---|
| 3,915,171 A | * | 10/1975 | Shermeta ................ 604/101.05 |
| 4,182,342 A |   | 1/1980 | Smith |
| 4,198,983 A | * | 4/1980 | Becker et al. ............... 128/349 |
| 4,455,691 A |   | 6/1984 | Van Aken Redinger et al. |
| 4,465,818 A |   | 8/1984 | Shirahata et al. |
| 4,543,089 A |   | 9/1985 | Moss |
| 4,604,412 A | * | 8/1986 | Joh et al. ..................... 523/112 |
| 4,666,433 A |   | 5/1987 | Parks |
| 4,685,901 A |   | 8/1987 | Parks |
| 4,701,163 A |   | 10/1987 | Parks |
| 4,834,721 A | * | 5/1989 | Onohara et al. ............ 604/266 |
| 4,959,054 A | * | 9/1990 | Heimke et al. ............. 604/175 |
| 5,007,900 A |   | 4/1991 | Picha et al. |
| 5,084,061 A | * | 1/1992 | Gau et al. ................... 606/195 |
| 5,356,391 A |   | 10/1994 | Stewart |
| 5,358,488 A |   | 10/1994 | Suriyapa |
| 5,439,443 A | * | 8/1995 | Miyata et al. ................ 604/96 |
| 5,519,082 A |   | 5/1996 | Yoshino |
| 5,681,914 A |   | 10/1997 | Kobayashi et al. |
| 5,997,503 A | * | 12/1999 | Willis et al. .................. 604/93 |

FOREIGN PATENT DOCUMENTS

WO PCT/US97/14804 3/1998

OTHER PUBLICATIONS

PCT Search Report dated Mar. 14, 2001.

* cited by examiner

Primary Examiner—Long V. Le
Assistant Examiner—Ann Y. Lam
(74) Attorney, Agent, or Firm—Dority & Manning, P.A.

(57) ABSTRACT

An improved gastrostomy feeding device with improved resistance to acidic and enzymatic degradation is disclosed. The device comprises an elongated feeding tube insertable through a patient's abdominal wall and an anchoring device mounted on the feeding tube, preferably near the first end, to retain said feeding tube within the stomach. The anchoring device is comprised of at least one internal retaining member fabricated from a trifluoropropyl or phenyl modified dimethylpolysiloxane elastomer having improved resistance to acids and enzymes.

24 Claims, 2 Drawing Sheets

SILICONE ELASTOMER MATERIAL FOR USE WITH ENTERIC FEEDING DEVICE

RELATED APPLICATIONS

The present application is based on a provisional application filed on Dec. 9, 1999 and having Ser. No. 60/170,000.

BACKGROUND OF THE INVENTION

Certain medical conditions require long term access to a person's stomach for the purpose of internal feedings and/or delivering medications. Often this is accomplished by inserting a gastrostomy device through an opening in the wall of the abdomen and into the stomach of a patient to supply nutrients and other fluids, including medications. Various types of gastrostomy devices have been installed in patients by means of percutaneous insertion, surgical placements, radiological placement or others. Once installed, these devices are retained in place by an internal retention member which functions to not only maintain the device in place but also to prevent leakage. Currently, there are several types of internal retention members on the market, e.g., molded or permanently attached flange elements, collar and balloon members, etc.

The particular materials to be utilized for internal retention members in a gastrostomy device must be biocompatible with the gastric environment. Such materials should also be resistant to acidic and enzymatic degradation in order to remain stable within the stomach for a long period of time, which reduces the frequency of replacement of the device and the risk of infection and trauma. In the past, the internal retention members have been made from elastomeric materials, such as latex materials or silicone elastomers. These materials have been found to be well suited for use in the construction of the internal retention members. The present invention, however, is directed to further improvements in internal retention members used in conjunction with a gastrostomy device. In particular, the present invention is directed to constructing internal retention members from materials that have improved resistance to acidic and/or enzymatic degradation when placed in the stomach of a patient.

SUMMARY OF THE INVENTION

The present invention is generally directed to a gastrostomy feeding device, such as a balloon catheter, that has improved resistance to acidic and enzymatic degradation when placed in the stomach of a patient. The gastrostomy feeding device includes an elongated feeding tube having a first end for insertion through a patient's abdominal wall and a second end including a feeding inlet. The device further includes an anchoring device mounted on the feeding tube to retain the feeding tube within the stomach. The anchoring device includes at least one internal retaining member. According to the present invention, the internal retaining member is made from a modified silicone elastomer.

For instance, the modified silicone elastomer can be a material made according to the following formula:

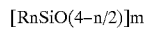

wherein n is 1-3, m>1, and R can be a methyl, alkyl, fluoroalkyl, phenyl, vinyl, alkoxy, or alkylamino group. If desired, the modified silicone elastomer can be endcapped with dimethylvinylsiloxane groups, trimethylsiloxy groups, methylphenylvinylsiloxy groups or hydroxyl groups. Further, the elastomer can contain a filler. Examples of fillers include metal oxides such as silica, pigments, processing aids, and the like.

In one particular embodiment of the present invention, the modified silicone elastomer is a fluoro modified polysiloxane. One example of a fluoro modified polysiloxane is a trifluoropropylsiloxane modified dimethylpolysiloxane. The fluoro modified polysiloxane can contain fluoro groups in an amount from about 5 mole percent to about 95 mole percent, and particularly from about 40 mole percent to about 60 mole percent.

In an alternative embodiment, the modified silicone elastomer can be a phenyl modified polysiloxane. When using a phenyl modified polysiloxane, for most applications, the modified polysiloxane should contain a relatively low amount of phenyl groups. For instance, the modified polysiloxane can contain phenyl groups in an amount less than about 50 mole percent, particularly in an amount less than 15 mole percent, and more particularly in an amount less than about 2 mole percent. In one embodiment, the phenyl modified polysiloxane is a diphenylsiloxane modified dimethylpolysiloxane.

Other features and aspects of the present invention are discussed in greater detail below.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Figure 1:
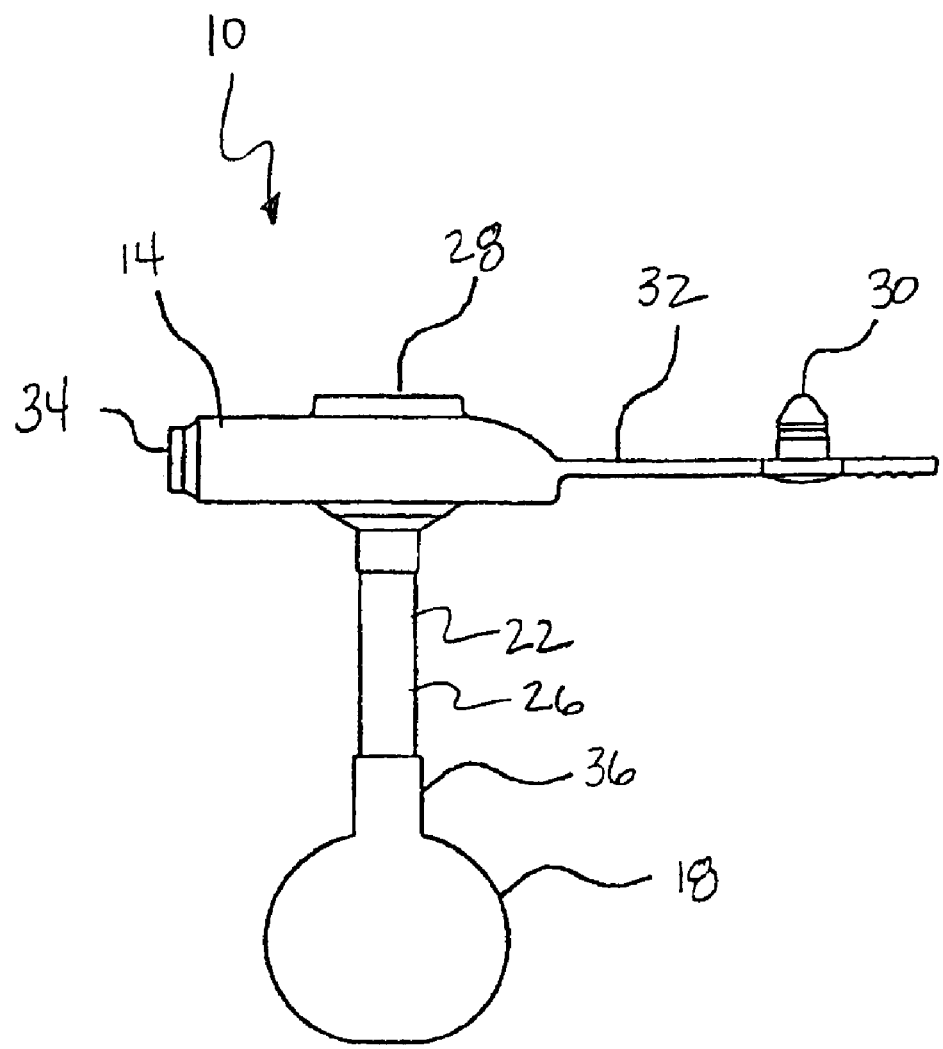
FIG. 1 is a side view of a balloon catheter that may be made in accordance with the teachings of the present invention with the balloon in an inflated configuration.

Repeated use of reference characters in the present specification and drawings is intended to represent same or analogous features or elements of the present invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention.

The present invention relates generally to a silicone elastomer anchoring device for use in enteric feeding systems. More particularly, this invention relates to the use of modified silicone elastomers such as fluoro modified or phenyl modified polysiloxanes as internal retaining members of an anchoring means to retain gastrostomy devices within the gastrointestinal tract. It has been found that internal retaining members made from the modified silicones have increased the resistance to acidic and enzymatic degradation when placed in the stomach of a patient.

There are three major types of silicones: fluids, resins and elastomers. For purposes of the present invention, the term "silicone" or "dimethicone" generally refers to polysiloxanes. Further, are used herein, a "modified silicone" refers to a broad family of more complex synthetic polymers containing a repeating silicon-oxygen backbone with organic side groups attached via carbon-silicon bonds. Such complex silicones, or polymeric siloxanes, may be linear, branched or cross-linked, and can be represented by the formula [RnSiO(4−n/2)]m, where n is 1-3, m>1, and R is methyl, longer chain alkyl, fluoroalkyl, phenyl, vinyl, alkoxy or alkylamino groups. The term modified silicone elastomers as used herein is also meant to include hetero- or copolymers of the above-described polysiloxanes.

Figure 2:
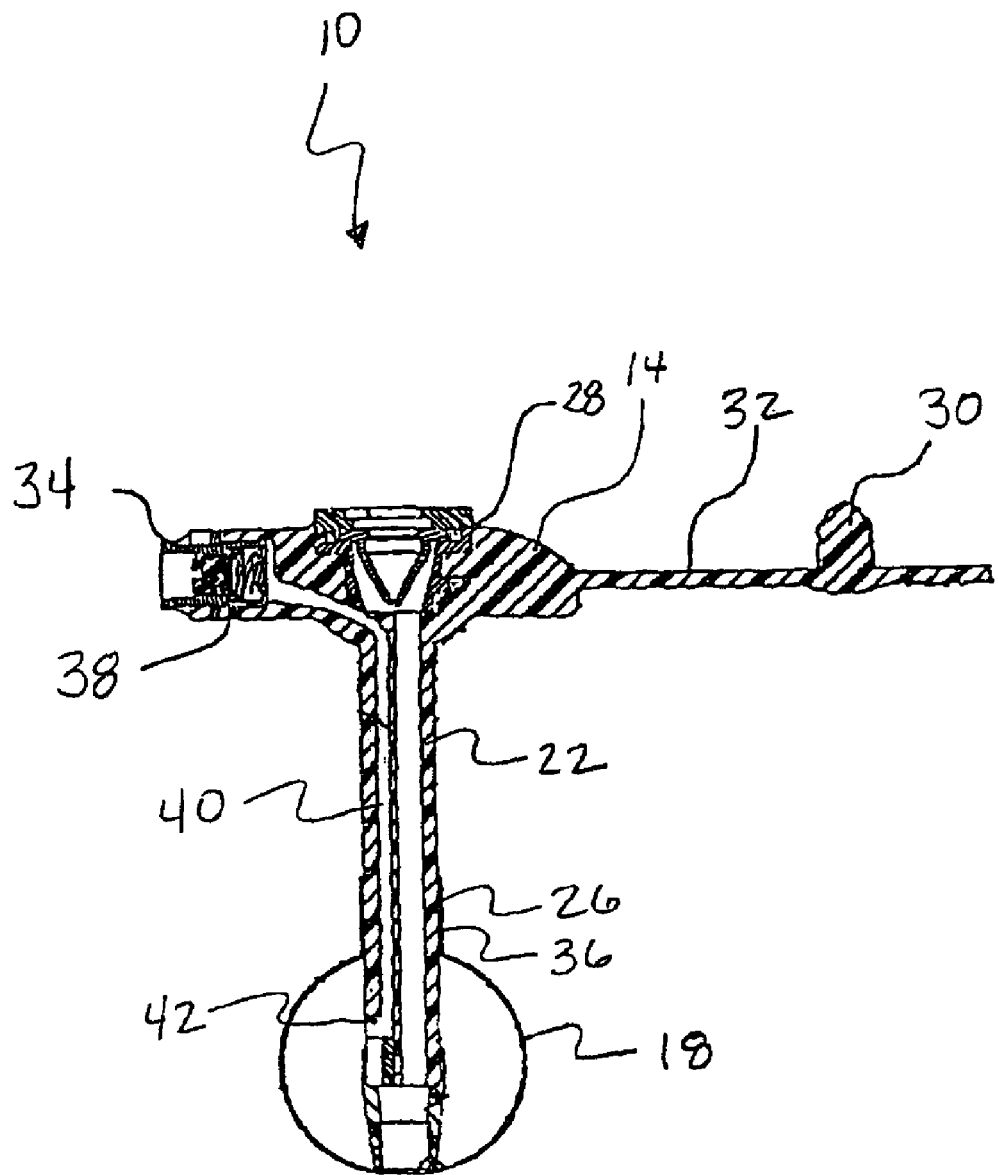
FIG. 2 is a cross-sectional view of the balloon catheter illustrated in FIG. 1.

Gastrostomy devices made in accordance with the present invention can come in various forms and constructions. For example, in one embodiment, the gastrostomy device made in accordance with the present invention can be a gastric balloon catheter generally 10 as shown in FIGS. 1 and 2. Balloon catheters of the type illustrated in the Figures are typically inserted into the gastrointestinal tract of a patient in order to insert substances into or to remove substances from the body. As shown, the balloon catheter 10 includes a head 14 disposed at a proximal end. The head 14 contains valves which regulate the flow of fluids through the balloon catheter. The head 14 also prevents the balloon catheter 10 from completely advancing through the stoma and into the stomach or intestine of the user.

To prevent the catheter from being pulled out of the stomach/intestinal wall, a balloon 18 is disposed along a catheter segment 22. The catheter segment 22 includes an elongate catheter shaft 26.

A first, central opening 28 in the head 14 enables the injection of enteral feeding solutions etc., through the catheter segment 22 and into the user. A plug 30 is disposed on a lanyard 32 which extends from the head 14. The plug 30 can be placed in the first, central opening 28 to prevent contamination of the catheter 10 when the opening is not being used to administer fluids through the catheter segment 22.

A second, side opening 34 serves as a port through which fluid may be injected into or removed from the balloon 18 through a lumen in the catheter segment 22. Thus, the second, side opening 34 enables the user to selectively control inflation and deflation of the balloon 18.

The balloon 18 includes a proximal cuff 36 which extends longitudinally along the catheter shaft 26 so as to be coaxial therewith. The balloon 18 also includes a distal cuff (not shown) which secures the distal end of the balloon to the catheter shaft 26.

The second, side opening 34 forms an inflation port in which a releasable one-way valve 38 is disposed as shown in FIG. 2. The releasable one-way valve 38 is disposed in communication with an inflation lumen 40 which runs through the catheter shaft 26 substantially parallel to a feeding lumen. The distal end of the inflation lumen 40 is in communication with a lateral opening 42. In this manner, application of fluid pressure (i.e. injection of air or saline solution) through the injection lumen 40 causes the fluid to fill the cavity of the balloon 18, thereby causing the balloon to inflate.

The balloon 18 is advantageous because it allows the catheter segment 22 to be inserted into the stoma while the balloon is uninflated. Once the catheter segment 22 is properly positioned in the stoma, a syringe is inserted into the side port 34 of the head 14 and a fluid is injected into the balloon 18 through the lumen 40. The fluid inflates the balloon so that it extends outwardly from the catheter shaft 26.

While the balloon 18 remains inflated, the catheter segment 22 stays properly positioned in the stoma. If the catheter segment 22 needs to be removed, the balloon 18 may be deflated so that it will not interfere with withdrawal of the catheter shaft 26.

As described above, the present invention is directed to constructing the balloon 18 or any other internal retaining member contained on a gastrostomy device with a modified silicone elastomer. The present inventor has discovered that the modified silicone elastomers of the present invention have improved burst strength and resistance to acidic and enzymatic degradation.

For example, in one embodiment of the present invention, the internal retaining member is made from a fluoro modified polysiloxane. For instance, the fluoro modified polysiloxane can be a trifluoropropyl modified polysiloxane, such as a trifluoropropylsiloxane modified dimethylpolysiloxane. A trifluoropropylsiloxane modified dimethylpolysiloxane can be synthesized by reacting methyl, 3,3,3-trifluoropropylsiloxane with dimethylsiloxane.

The fluoro modified polysiloxane can contain from about 5 mole percent to about 95 mole percent, and particularly from about 40 mole percent to about 60 mole percent of fluoro groups, such as trifluoropropylsiloxane units. In one embodiment, the internal retaining member of the present invention can be made from a trifluoropropylsiloxane modified dimethylpolysiloxane containing 50 mole percent trifluoropropylsiloxane units. Such fluoro modified polysiloxane elastomers are commercially available from NuSil Technologies under various trade names including MED 12-6650.

Besides using fluoro modified polysiloxanes, in an alternative embodiment, the present invention is directed to using phenyl modified polysiloxanes, and particularly phenyl modified polysiloxanes that have a relatively low phenyl content (less than about 50 mole percent). For example, in one embodiment, the phenyl modified polysiloxane can be a diphenyl modified polysiloxane, such as a diphenylsiloxane modified dimethylpolysiloxane. Such phenyl modified polysiloxanes are commercially available from NuSil Technologies under various trade names including MED 10-6400, MED 10-6600, MED 12-6400, and 12-6600.

For most applications, the phenyl modified polysiloxane should contain phenyl units in an amount from about 0.5 mole percent to about 50 mole percent, particularly in an amount less than about 25 mole percent, and more particularly in an amount less than about 15 mole percent. In one particular embodiment, a diphenylsiloxane modified dimethylpolysiloxane can be used that contains diphenylsiloxane units in an amount less than about 5 mole percent, and particularly in an amount less than about 2 mole percent. The diphenylsiloxane modified dimethylpolysiloxane can be synthesized by reacting diphenylsiloxane with dimethylsiloxane.

The particular elastomers described above are meant to include hetero- or copolymers formed from polymerization or copolymerization of dimethylsiloxane cyclics and diphenylsiloxane cyclics or trifluoropropylsiloxane cyclics with appropriate endcapping units. Endcapping units that may be used include dimethylvinylsiloxane units, trimethylsiloxy units, methylphenylvinylsiloxy units, hydroxyl units, or mixtures thereof. Hence, the terms diphenyl or trifluoropropyl modified dimethylpolysiloxanes and copoloymers of diphenylpolysiloxane or trifluoropropylpolysiloxane and dimethylpolysiloxane may be used interchangeably. It is also contemplated that the modified silicone elastomers may also be a reaction product of dimethylpolysiloxane and a combination of fluoro groups and phenyl groups, such as a combination of diphenylpolysiloxane and trifluoropropylpolysiloxane.

The modified silicone elastomers may also contain fillers, such as reinforcing silica, processing aids, additives and pigments as is conventional in the art.

The invention will now be illustrated by the following examples which are not intended to be limiting in any way. These examples illustrate the preferred embodiments of the invention that are currently known. However, other embodiments may be made within the scope of the disclosure. All references cited are incorporated herein by reference in their entirety.

EXAMPLES

Example 1

In this example, sterile gastrostomy tubes were made for both the control and the test group. The control group balloons were made from conventional organopolysiloxane. Specifically, the control group balloons were made from a silicone dispersion containing an organopolysiloxane obtained from Applied Silicone Corporation of Ventura, Calif. having Part No. 40,000. The test group balloons were made from phenyl modified organo silicone elastomer sold under the trade name of MED 10-6400 and which is commercially available from NuSil Technology. Additionally, the devices were made at various diameters, e.g., 14 FR (one FR is equivalent to about ⅓ mm), 18 Fr, and 24 Fr. The structure and method of making such devices is well known in the art.

A typical gastrostomy tube comprises an inflatable balloon, which is glued to a feeding tube, and can be made by conventional extrusions and injection molding techniques. A visual inspection was performed on all balloons to determine whether each balloon exhibited proper symmetry and whether each balloon was clear and smooth. All balloons were also inspected for functionality by inflation, i.e., testing whether each balloon would fail upon inflation. All control and test samples passed the visual and functional inspection requirement prior to further testing.

Example 2

In this example, a balloon burst strength study was performed on the gastrostomy devices prepared in Example 1. The control group balloons were made from the conventional organopolysiloxane and the test group balloons were made from the phenyl modified silicone elastomer of Example 1.

Twenty of each sample group (see Table 1) were inflated with 10 cc of saline. The devices were then submerged in a gastric solution for various periods of time according to the size of the device, i.e. 48 hrs for 14 Fr sizes, 96 hrs for 18 Fr sizes, and 192 hrs for 24 Fr sizes. The devices were removed from the solution, rinsed, and then inflated with 0.9 N saline until tube failure occurred. The acceptance standard for balloon burst strength is that the test groups could not burst at a lower volume than that of the control groups. Both these variables may be compared in Table 1 below.

TABLE 1

Balloon Burst Strength Study

| Sample Group | Mean Burst Volume | % of Samples (Failure Mode- Bust) | % of Samples (Failure Mode- Cuff Failure |
|---|---|---|---|
| 14 Fr Control Group | 36.30 cc | 100% | 0% |
| 14 Fr Phenyl Group | 44.45 cc | 100% | 0% |
| 18 Fr Control Group | 29.06 cc | 100% | 0% |
| 18 Fr Phenyl Group | 58.90 cc | 100% | 0% |
| 24 Fr Control Group | 80.16 cc | 100% | 0% |
| 14 Fr Phenyl Group | 119.50 cc | 100% | 0% |

The results summarized in Table 1 show that the gastrostomy balloons made from the phenyl content silicone elastomers were stronger than the respective control groups because their burst volumes were significantly higher. For example, for the 14 Fr devices, the mean burst volume of the phenyl group was 44.45 cc, which is about 22% higher than the mean burst volume of the control group, which was 36.30 cc. Similarly, the burst strength of the phenyl group is 100% higher for 18 Fr device, and 50% higher for 24 Fr device, compared to the respective control group.

Example 3

In this example, the gastrostomy tubes prepared according to Example 1, were tested in a high acid solution to examine the functioning life of the balloon in a simulated gastric environment (about pH 1.2). The control group tubes were made from the conventional organopolysiloxane, and the test group tubes were made from the phenyl content silicone elastomer of Example 1.

Thirty-two of each sample group (see Table 2) were tested for high acid resistance in a simulated gastric solution, which is about pH 1.2. Balloons were monitored at 24 hr intervals for failures such as a balloon burst, cuff failure, or pinhole leaks. At the point of failure, the balloons were removed from the gastric solution. The time when failure occurred for each tube tested was recorded along with the failure mode. The results are summarized in Table 2.

| Sample Group | Days to 10% Failure | Days to 50% Failure | Days to 100% Failure |
|---|---|---|---|
| 14 Fr Control Group | 3 | 4 | 28 |
| 14 Fr Phenyl Group | 21 | 34 | 54 |
| 18 Fr Control Group | 4 | 4 | 10 |
| 18 Fr Phenyl Group | 25 | 45 | 72 |
| 24 Fr Control Group | 19 | 21 | 62 |
| 24 Fr Phenyl Group | 65 | 144 | not available |

The results shown in Table 2 indicate that the gastrostomy tubes made from the phenyl silicone elastomer lasted longer in a high acid solution compared with the control group. Therefore, the gastrostomy tubes made from the phenyl silicone elastomer provide for stronger acid resistance compared to conventional tubes.

Example 4

In this example, gastrostomy tubes were made for both the control and the test group. The control group balloons were made from the conventional organopolysiloxane. The test group balloons were made from a trifluoropropyl modified organo silicone elastomer sold under the trade name of MED 12-6650 and which is commercially available from NuSil Technology. The devices were made in 18FR diameter.

The devices were tested in a simulated gastric environment as in Example 3. The trifluoropropyl modified organo silicone elastomer balloons exhibited at least a 100% life extension as compared to the control samples.

In summary, the above examples show that the gastrostomy tubes made from a phenyl silicone elastomer had the same visual and functional properties as the control group. However, the gastrostomy tubes made from phenyl and/or trifluoropropyl modified silicone elastomers according to the present invention were stronger than the conventional tubes in burst strength tests. In addition, the phenyl and/or trifluoropropyl modified silicone elastomer devices of the present invention also lasted longer in a strong acid solution than the respective control groups in life tests. Therefore, these examples have shown that the phenyl and trifluoropropyl modified silicone gastrostomy devices are acid resistant and have higher burst strength than the conventional devices.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A gastrostomy feeding device having improved resistance to acidic and enzymatic degradation comprising an elongated feeding tube having a first end for insertion through a patient's abdominal wall and a second end including a feeding inlet, and an anchoring means mounted on the feeding tube to retain said feeding tube within the stomach, wherein said anchoring means has at least one internal retaining member comprised of a modified silicone elastomer selected from the group consisting of trifluoropropylsiloxane modified dimethylpolysiloxane, diphenylsiloxane modified dimethylpolysiloxane, and combinations thereof.

2. The gastrostomy feeding device according to claim 1, wherein said modified silicone elastomer is a trifluoropropylsiloxane modified dimethylpolysiloxane.

3. The gastrostomy feeding device according to claim 2, wherein the trifluoropropylsiloxane content of said elastomer is from about 5 to 95 mole percent.

4. The gastrostomy feeding device according to claim 3, wherein the trifluoropropylsiloxane content of said elastomer is from about 40 to 60 mole percent.

5. The gastrostomy feeding device according to claim 1, wherein said modified silicone elastomer is a diphenylsiloxane modified dimethylpolysiloxane.

6. The gastrostomy feeding device according to claim 5, wherein the diphenylsiloxane content of said elastomer is from about 0.5 to 50 mole percent.

7. The gastrostomy feeding device according to clam 6, wherein the diphenylsiloxane content of said elastomer is from about 10 to 25 mole percent.

8. The gastrostomy feeding device according to claim 5, wherein the diphenylsiloxane content of the elastomer is less than about 10 mole percent.

9. The gastrostomy feeding device according to claim 5, wherein the diphenylsiloxane content of the elastomer is less than about 2 mole percent.

10. A gastrostomy feeding device having improved resistance to acidic and enzymatic degradation comprising an elongated feeding tube having a first end for insertion through a patient's abdominal wall and a second end including a feeding inlet, and an anchoring means mounted on the feeding tube to retain said feeding tube within the stomach, wherein said anchoring means has at least one internal retaining member comprised of a modified silicone elastomer selected from the group consisting of phenyl-modified silicone, fluoro-modified silicone, and combinations thereof, wherein the modified silicone elastomer is endcapped with a material selected from the group consisting of dimethylvinylsiloxane groups, trimethylsiloxy groups, methylphenylvinylsiloxy groups and hydroxyl groups.

11. A gastrostomy feeding device comprising:

an elongated feeding tube having a first end for insertion through a patient's abdominal wall and a second end including a feeding inlet, and an internal retaining member for retaining the feeding tube within the stomach, said internal retaining member comprised of a fluoro modified polysiloxane.

12. A gastrostomy feeding device according to claim 11, wherein said fluoro modified polysiloxane comprises a trifluoropropylsiloxane modified dimethylpolysiloxane.

13. A gastrostomy feeding device as defined in claim 12, wherein the fluoro modified polysiloxane contains trifluoropropylsiloxane in an amount from about 40 mole percent to about 60 mole percent.

14. A gastrostomy feeding device as defined in claim 11, wherein said polysiloxane comprises a dimethylpolysiloxane.

15. A gastrostomy feeding device as defined in claim 11, wherein the fluoro modified polysiloxane contains from about 40 mole percent to about 60 mole percent fluoro groups.

16. A gastrostomy feeding device as defined in claim 11, wherein the fluoro modified polysiloxane is endcapped with a material selected from the group consisting of dimethylvinylsiloxane groups, trimethylsiloxy groups, methylphenylvinylsiloxy groups and hydroxyl groups.

17. A gastrostomy feeding device as defined in claim 11, wherein said fluoro modified polysiloxane contains a filler.

18. A gastrostomy feeding device comprising:

an elongated feeding tube having a first end for insertion through a patient's abdominal wall and a second end including a feeding inlet, member for retaining the feeding tube within the stomach, said internal retaining member comprised of a phenyl modified polysiloxane, said phenyl modified polysiloxane containing phenyl groups in an amount less than about 25 mole percent.

19. A gastrostomy feeding device as defined in claim 18, wherein the phenyl modified polysiloxane comprises a diphenylsiloxane modified dimethylpolysiloxane.

20. A gastrostomy feeding device as defined in claim 19, wherein said phenyl modified polysiloxane contains diphenylsiloxane groups in an amount less than about 2 mole percent.

21. A gastrostomy feeding device as defined in claim 18, wherein said polysiloxane comprises dimethylpolysiloxane.

22. A gastrostomy feeding device as defined in claim 18, wherein said phenyl modified polysiloxane contains phenyl groups in an amount less than about 2 mole percent.

23. A gastrostomy feeding device as defined in claim 18, wherein the phenyl modified polysiloxane is endcapped with a material selected from the group consisting of dimethylvinylsiloxane groups, trimethylsiloxy groups, methylphenylvinylsiloxy groups and hydroxyl groups.

24. A gastrostomy feeding device as defined in claim 18, wherein said phenyl modified polysiloxane contains a filler.

* * * * *

UNITED STATES PATENT AND TRADEMARK OFFICE
CERTIFICATE OF CORRECTION

PATENT NO. : 6,923,786 B2
DATED : August 2, 2005
INVENTOR(S) : Cameron G. Rouns, Don J. McMichael and Michael A. Kenowski It is certified that error appears in the above-identified patent and that said Letters Patent is hereby corrected as shown below:

Column 7,
Line 54, "clam" should be -- claim --.

Column 8,
Line 42, "including a feeding inlet, member for retaining the" should be -- including a feeding inlet, and an internal retaining member for retaining the --.

Signed and Sealed this

Third Day of January, 2006

JON W. DUDAS
*Director of the United States Patent and Trademark Office*